United States Patent
Henderson et al.

(10) Patent No.: US 10,777,312 B2
(45) Date of Patent: *Sep. 15, 2020

(54) DYNAMIC CRITICAL ACCESS OVERRIDE FOR MEDICATION DISPENSING APPARATUSES

(71) Applicant: CERNER INNOVATION, INC., Kansas City, KS (US)

(72) Inventors: Todd Reed Henderson, Leawood, KS (US); Mark David Gromowsky, Kansas City, MO (US); Jonathan Dion Meisel, Kansas City, MO (US); John Michael Mortimer, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,563

(22) Filed: Jun. 17, 2019

(65) Prior Publication Data

US 2019/0304583 A1 Oct. 3, 2019

Related U.S. Application Data

(63) Continuation of application No. 14/852,216, filed on Sep. 11, 2015, now Pat. No. 10,366,209, which is a
(Continued)

(51) Int. Cl.
*G16H 20/13* (2018.01)
*G07F 17/00* (2006.01)
(Continued)

(52) U.S. Cl.
CPC ......... *G16H 20/13* (2018.01); *G06F 19/3456* (2013.01); *G06F 19/3462* (2013.01);
(Continued)

(58) Field of Classification Search
CPC . G06F 19/3462; G06F 19/3456; G06Q 50/24; G07F 17/0092; G16H 20/13; G16H 10/60; G16H 20/10
(Continued)

(56) References Cited

U.S. PATENT DOCUMENTS 5,036,462 A 7/1991 Kaufman et al.
5,084,828 A 1/1992 Kaufman et al.
(Continued)

OTHER PUBLICATIONS

Final Office Action received for U.S Appl. No. 13/401,589, dated Apr. 15, 2013, 11 pages.
(Continued)

*Primary Examiner* — Michael Collins
(74) *Attorney, Agent, or Firm* — Shook, Hardy & Bacon LLP

(57) ABSTRACT

A critical access override list may be generated dynamically based on patient profile information for a single patient or a group of patients. A single patient or group of patients is initially identified. Patient profile information for the patient or group of patients is accessed. The patient profile information is analyzed, and medications are selected for critical access override. The selected medications are added to a critical access override list available to a medication dispensing apparatus to provide quicker access to the medications for emergency situation purposes via critical access override dispensing in which fewer steps are performed than normal medication dispensing events.

20 Claims, 4 Drawing Sheets

Related U.S. Application Data continuation of application No. 13/401,589, filed on Feb. 21, 2012, now Pat. No. 9,195,802.

(51) Int. Cl.
  *G06F 19/00* (2018.01)
  *G06Q 50/24* (2012.01)
  *G16H 10/60* (2018.01)
  *G16H 20/10* (2018.01)

(52) U.S. Cl.
  CPC ......... *G06Q 50/24* (2013.01); *G07F 17/0092* (2013.01); *G16H 10/60* (2018.01); *G16H 20/10* (2018.01)

(58) Field of Classification Search
  USPC .................................................. 700/231–244
  See application file for complete search history.

(56) References Cited

U.S. PATENT DOCUMENTS

| | | | |
|---|---|---|---|
| 5,126,957 A | 6/1992 | Kaufman et al. | |
| 5,267,174 A | 11/1993 | Kaufman et al. | |
| 6,175,779 B1 * | 1/2001 | Barrett ................. | A61G 12/001 700/242 |
| 6,650,964 B2 | 11/2003 | Spano et al. | |
| 6,671,579 B2 | 12/2003 | Spano et al. | |
| 7,155,306 B2 | 12/2006 | Haitin et al. | |
| 7,509,264 B2 | 3/2009 | Hasan et al. | |
| 7,706,915 B2 | 4/2010 | Mohapatra et al. | |
| 7,865,263 B2 | 1/2011 | Spano et al. | |
| 8,756,250 B2 | 6/2014 | Unger et al. | |
| 9,195,802 B2 * | 11/2015 | Henderson ............. | G16H 20/13 |
| 10,366,209 B2 * | 7/2019 | Henderson ............. | G16H 10/60 |
| 2003/0195655 A1 | 10/2003 | Spano et al. | |
| 2005/0055242 A1 | 3/2005 | Bello et al. | |
| 2005/0107913 A1 * | 5/2005 | Engleson ............... | G06Q 50/22 700/237 |
| 2006/0149416 A1 | 7/2006 | Mohapatra et al. | |
| 2006/0271405 A1 | 11/2006 | Cipolle et al. | |
| 2007/0088461 A1 | 4/2007 | Haitin et al. | |
| 2008/0262870 A1 | 10/2008 | Jones et al. | |
| 2008/0319581 A1 | 12/2008 | Vahlberg et al. | |
| 2011/0071667 A1 | 3/2011 | Spano et al. | |
| 2013/0218329 A1 | 8/2013 | Henderson et al. | |
| 2015/0379236 A1 | 12/2015 | Henderson et al. | |

OTHER PUBLICATIONS

Final Office Action received for U.S Appl. No. 13/401,589, dated Mar. 3, 2015, 11 pages.

Final Office Action received for U.S Appl. No. 14/852,216, dated Feb. 7, 2018, 22 pages.

Final Office Action received for U.S Appl. No. 14/852,216, dated Nov. 4, 2016, 15 pages.

Greene et al., "Greene, et al. Maximizing the Efficiencies of ADC's", Available Online at <http://www.pppmag.com/article_print_php?articleid=896>, Aug. 17, 2011, 2 pages.

Holder et al., "Establishing and Managing an ADM Override Compliance System, Pharmacy Purchasing", Apr. 2007, pp. 14-17.

Issue Notification received for U.S. Appl. No. 14/852,216, dated Jul. 10, 2019, 1 page.

Non Final Office Action received for U.S Appl. No. 13/401,589, dated Aug. 19, 2014, 12 pages.

Non Final Office Action received for U.S Appl. No. 13/401,589, dated Oct. 1, 2012, 10 pages.

Non Final Office Action received for U.S Appl. No. 14/852,216, dated Mar. 1, 2016, 13 pages.

Non Final Office Action received for U.S Appl. No. 14/852,216, dated Jul. 3, 2017, 14 pages.

Notice of Allowance received for U.S Appl. No. 13/401,589, dated Jul. 17, 2015, 5 pages.

Notice of Allowance received for U.S Appl. No. 14/852,216, dated May 15, 2019, 8 pages.

* cited by examiner

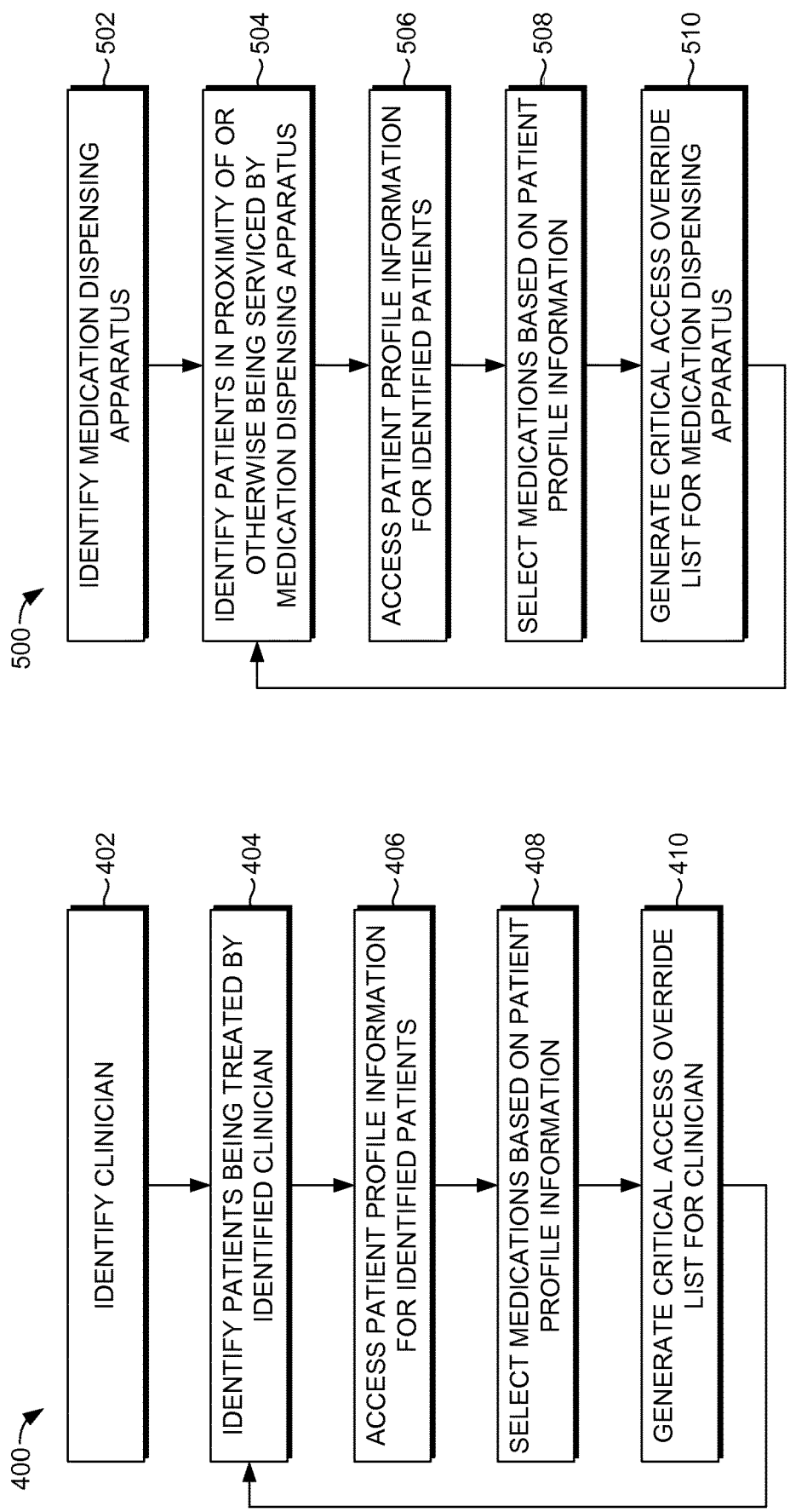

DYNAMIC CRITICAL ACCESS OVERRIDE FOR MEDICATION DISPENSING APPARATUSES

RELATED APPLICATION

This patent application is a continuation of U.S. application Ser. No. 14/852,216, filed Sep. 11, 2015, which is a continuation of U.S. application Ser. No. 13/401,589, filed Feb. 21, 2012, and issued as U.S. Pat. No. 9,195,802, each of which is incorporated herein by reference in the entirety.

BACKGROUND

Many hospitals include a hospital pharmacy department that is responsible for dispensing medications to patients in various areas of the hospitals. In some hospitals, the medications are dispensed in a distributed environment with a central pharmacy (or multiple "central" pharmacies) and a number of medication dispensing apparatuses (e.g., medication dispensing cabinet) remotely situated in various locations throughout the hospital. The remotely-located medication dispensing apparatuses allow medications to be stored and dispensed closer to the location of patient care, which may provide a number of benefits, including simplifying and speeding up the process of clinicians obtaining medications for their patients.

The typical process of dispensing medications from medication dispensing apparatuses includes a number of steps, such as requiring identification of the clinician dispensing the medications, identification of the patient for which the medications are dispensed, medication interaction checking, allergy checking, duplicate checking, medication counting, and other pharmacy verification. These steps are typically required for a variety of reasons, including patient safety, controlling the dispensing of medications, and auditing purposes, to name a few.

This process of obtaining medications from a medication dispensing apparatus is acceptable in normal medication administrations for patients. However, there are some emergency situations in which the process may be unacceptably slow. Crash carts are often stocked with a limited set of drugs to provide quick access for dire patient situations, but there are a number of other emergency situations that occur in hospitals that do not require a crash cart or require medications not included in a crash cart.

BRIEF SUMMARY

Embodiments of the present invention relate to dynamically generating critical access override lists for individual patients or groups of patients based on patient profile information. The critical access override lists include a list of medications that may be dispensed from a medication dispensing apparatus using a critical access override dispensing process in which fewer steps are required than a typical medication dispensing event to provide for quick access to medications in emergency situations.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein:

FIG. 4 is a flow diagram showing a method for dynamically generating a critical access override list for a group of patients corresponding with a particular clinician in accordance with another embodiment of the present invention;

FIG. 5 is a flow diagram showing a method for dynamically generating a critical access override list for a group of patients corresponding with a particular medication dispensing apparatus in accordance with an embodiment of the present invention.

DETAILED DESCRIPTION

Figure 1:
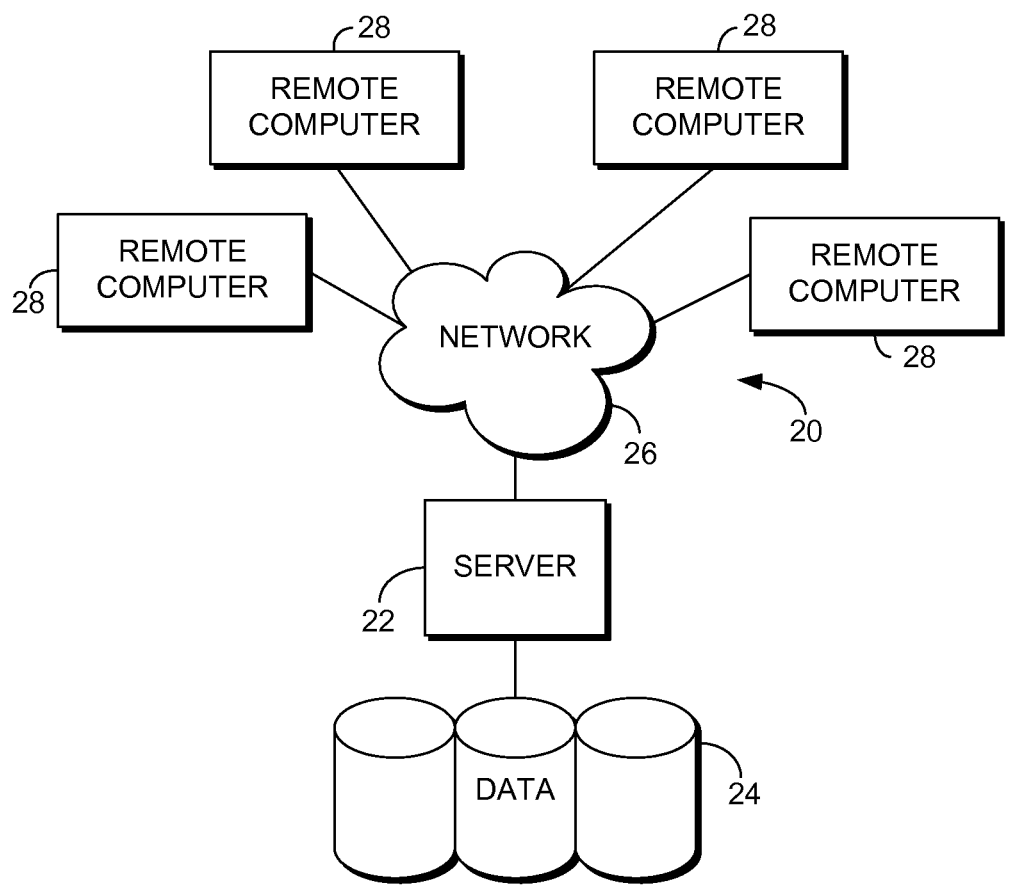
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide for dynamic critical access override lists for mediation dispensing apparatuses. As used herein, a "critical access override list" is a list of one or more medications that may be dispensed from a medication dispensing apparatus without requiring all of the steps required for a typical medication dispensing event from the medication dispensing apparatus. For instance, a medication on the critical access override list may be dispensed without requiring interaction checking, allergy checking, duplicate therapy checking, counting, and/or other steps typically performed during a normal medication dispensing event from a medication dispensing apparatus. Critical access override is based on some emergency situations warranting quick access to certain drugs that overrides some of the patient safety and other considerations of the typical medication dispensing process. The actual steps required and steps not required during a critical access override dispensing event may be configurable and defined by hospital policies in accordance with embodiments of the present invention.

Some embodiments of the present invention may provide for dynamic critical access override lists by employing real-time patient profile information to determine the medications to include in the critical access override lists. The patient profile information may generally include any piece of patient information that may be useful in determining which medications the patient is likely to need in emergency situations. By way of example only and not limitation, the patient profile information may include a primary diagnosis, a secondary or other diagnosis, current medications, allergies, age, gender, and ethnicity.

In accordance with some embodiments, a personalized critical access override list may be generated for a single patient. Generally, patient profile information may be accessed for the patient, and medications may be selected for the personalized critical access override list for that patient. By accessing and analyzing patient profile information for the patient, medications that are likely to be needed for the patient in emergency situations may be identified and those medications may be added to a critical access override list to allow for quick access to those medications.

By way of example to illustrate, suppose that a patient has a particular allergy documented in the patient profile information for the patient. When the system accesses the patient profile information, the system may identify that the patient has the allergy and may add diphenhydramine, 25 mg tablets and epinephrine, 0.3 mg vial to the patient's critical access override list as these medications may be needed for the patient if the patient suffers an allergic reaction.

As additional examples, the system may add drug reversal or rescue agents if the patient has a target drug documented in the patient's patient profile information. For instance, the system may add flumanzenil, 1 mg/10 mL vial to the patient's critical access override list as a reversal or rescue agent for a benzodiazepine (e.g., Valium) overdose if the patient is prescribed a benzodiazepine. The system could also add naloxone, 1 mg vial as a reversal agent for an opioid (e.g., morphine) overdose if the patient is prescribed an opioid.

As further examples, the system may add emergent drugs for diagnosis dependent overrides. For instance, if the patient is a diabetic, the system may add regular insulin to the patient's critical access override list. If the patient's patient profile information indicates that the patient has angina, the system could add nitroglycerin, 4 mg tablet to the patient's critical access override list.

In further embodiments of the invention, a critical access override list may be generated for a group of patients. Generally, a group of patients may be identified, patient profile information accessed for each patient in the group, and medications selected to generate a critical access override list for the group. This may be useful in situations in which a single critical access override list for a group of patients may be more convenient than multiple lists for each patient. For example, a critical access override list may be generated for a clinician based on the group of patients being treated by that clinician. Accordingly, when the clinician accesses a medication dispensing apparatus, critical access overrides may be provided for medications for each of the patients being treated by the clinician.

As another example of providing a critical access override list for a group of patients, a critical access override list may be generated for a medication dispensing apparatus for all patients identified as being associated with the medication dispensing apparatus. This may include patients who are likely to have their medications dispensed by that medication dispensing apparatus. For instance, all patients within a certain proximity to the medication dispensing apparatus may be identified and the patient profile information for those patients may be used to generate the critical access override list for the medication dispensing apparatus.

The process of generating a critical access override list for a patient or group of patients may be done locally at a medication dispensing apparatus or elsewhere, for instance, at the backend of a healthcare facility's medical information computing system. Additionally, a critical access override list may be generated at the time of dispensing medications or may be performed as a background process independent of any medication dispensing event. For instance, the critical access override list may be update on a scheduled basis (e.g., hourly, daily, weekly, etc.) or based on some other triggering event (e.g., changes in patient profile information).

Medications dynamically selected for critical access override in accordance with embodiments of the present invention may be included in a standalone critical access override list. Alternatively, the dynamically-selected medications may be included with a standard list of medications for critical access override that may be statically defined, for instance, for a healthcare facility, care unit, or medication dispensing apparatus.

Auditing of critical access override dispensing events may be provided in accordance with some embodiments. In particular, the system may be configured to track when critical access overrides are performed by clinicians and generate reports. As such, information may be available to ensure that critical access overrides are not being improperly used by certain clinicians.

Referring now to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
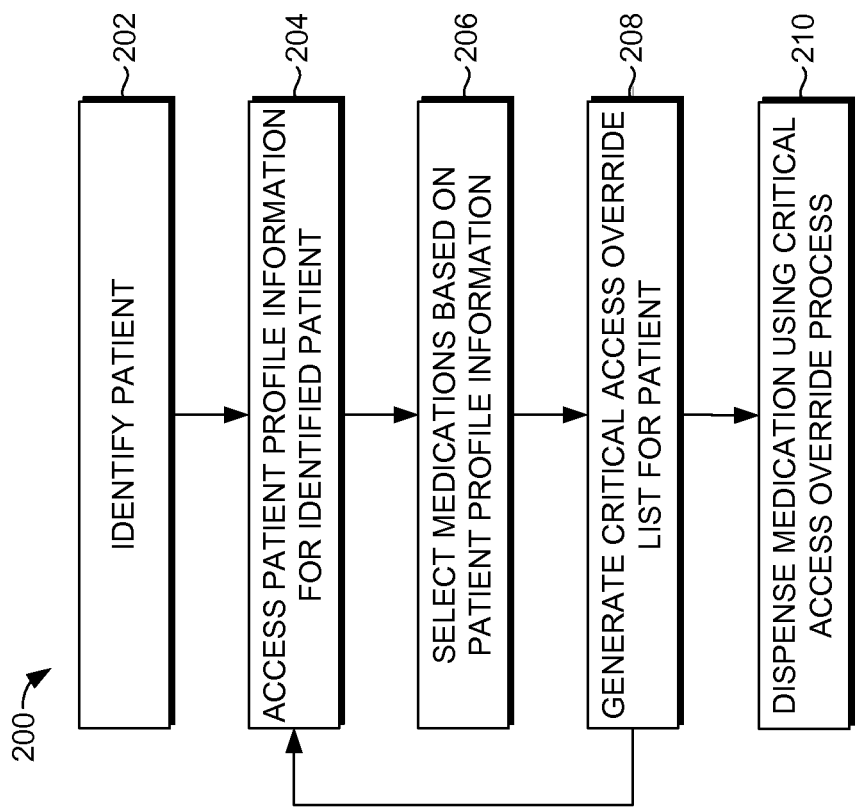
FIG. 2 is a flow diagram showing a method for dynamically determining medications for a critical access override list for a particular patient in accordance with an embodiment of the present invention.

Turning now to FIG. 2, a flow diagram is provided that illustrates a method 200 for dynamically determining medications for a critical access override list for a particular patient in accordance with an embodiment of the present invention. As shown at block 202, a patient is initially identified. In some embodiments, this may be done when a medication dispensing event is initiated for a patient. For instance, a clinician may access a medication dispensing apparatus and identify the patient (e.g., by manually entering patient information or scanning a patient ID barcode or other indicia associated with a patient) for which medications are to be dispensed. In other embodiments, the method 200 may be performed as a background process independent of any medication dispensing event for the patient. In such embodiments, the system may identify the patient for dynamically determining medications for the patient's personalized critical access override list on a periodic basis (e.g., hourly, daily, etc.) or when there is some other triggering event (e.g., a change to the patient's electronic medical record). In some instances, any change to the patient's electronic medical record may prompt the system to update the patient's personalized critical access override list; while in other instances, only certain changes to the patient's electronic medical record may prompt the system to update the patient's personalize critical access override list.

As shown at block 204, patient profile information is accessed. The patient profile information may be stored at and accessed from a variety of different locations in accordance with various embodiments of the present invention. By way of example only and not limitation, the patient profile information may be stored locally at a medication dispensing apparatus and/or may be stored in an electronic medical record for the patient at a centralized data store. The patient profile information accessed at block 204 may include any of a variety of different medically-related information for the patient that may be used to determine medications for critical access override for the patient (i.e., any medications that may be needed for the patient in an emergency situation). For instance, the patient profile information may include a primary diagnosis, a secondary or other diagnosis, current medications, allergies, age, gender, and ethnicity.

One or more medications are selected for critical access override for the patient based on the patient profile information, as shown at block 206. Generally, the system may analyze the patient profile information to predict what medications may be needed for the patient in an emergency situation.

The one or more medications are added to a personalized critical access override list for the patient, as shown at block 208. In some instances, this may include generating a new critical access override list for the patient based on the identified one or more medications. In other instances, the one or more medications identified at block 206 are added to a standard critical access override list to create the personalized critical access override list for the patient. The standard critical access override list may include a list of standard medications for which critical access override is provided as defined for a particular healthcare facility, a care unit, a particular medication dispensing apparatus, or other basis of standardization. In further embodiments, the one or more medications identified at block 206 are used to update an existing personalized critical access override list for the patient. For instance, the personalized critical access override list for the patient may be updated on a scheduled basis or based on some other triggering event (e.g., change in the patient profile information). Updating a critical access override list may include adding and/or removing medications from the list. Any and all such combinations and variations are contemplated to be within the scope of embodiments of the present invention.

As noted above, the process of selecting medications for a critical access override list for a particular patient may be repeated as shown by the return to block 204 from block 208. For instance, the process may be performed on a periodic basis (e.g., hourly, daily, etc.) or when there is some other triggering event (e.g., a change to the patient's electronic medical record). When the process is repeated, new medications may be identified for patient's personalized critical access override list and/or medications previously identified based on previous patient profile information may be removed based on the patient's current patient profile information. For example, if a drug reversal or rescue agent was previously added to the critical access override list based on a target drug being on the patient's profile information, if that target drug is removed from the patient's profile information, the drug reversal or rescue agent may be removed from the patient's critical access override list.

As shown at block 210, after the critical access override list has been generated, a medication from the critical access override list may be selected for dispensing using a critical access override process.

Figure 3:
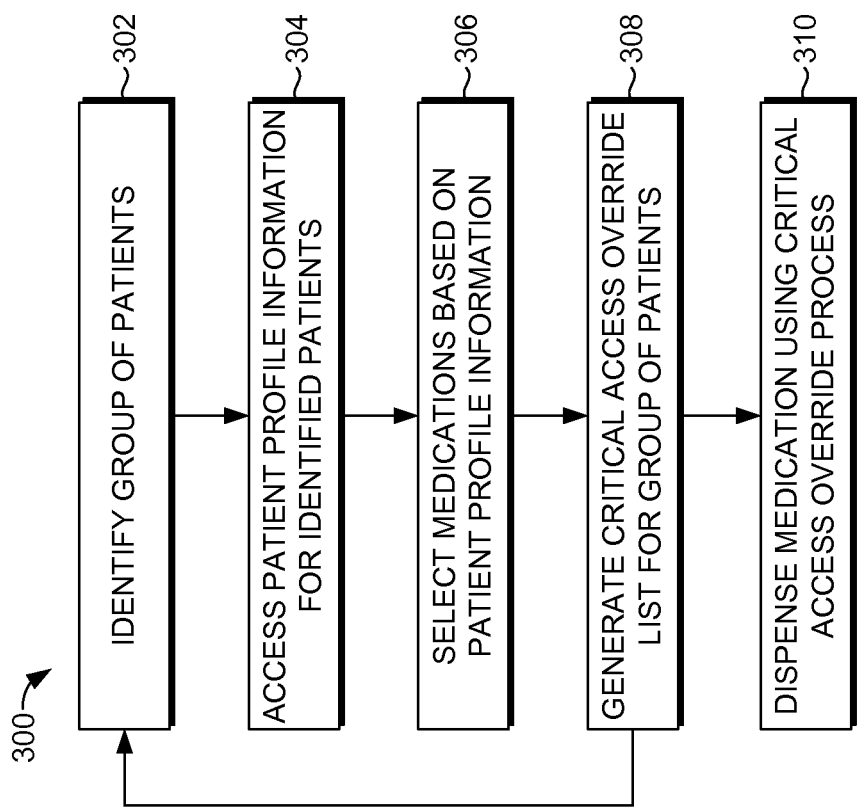
FIG. 3 is a flow diagram showing a method for dynamically generating a critical access override list for a group of patients in accordance with an embodiment of the present invention.

With reference now to FIG. 3, a flow diagram is provided that illustrates a method 300 for dynamically generating a critical access override list for a group of patients in accordance with an embodiment of the present invention. As shown at block 302, a group of patients is identified. The group of patients may be identified in any of a variety of different manners. For instance, as will be described in further detail below with reference to FIG. 4, the group of patients may be associated with a particular clinician. As another example that will be described in further detail below with reference to FIG. 5, the group of patients may be associated with a particular medication dispensing apparatus. It should be understood that these are only two specific examples of how patients may be grouped for purposes of dynamically generating critical access override lists, and other approaches for grouping patients may be employed within the scope of embodiments of the present invention.

Patient profile information for each patient from the group of patients is accessed, as shown at block 304. The patient profile information for the group of patients may be stored at and accessed from a variety of different locations in accordance with various embodiments of the present invention. By way of example only and not limitation, the patient profile information may be stored locally at a medication dispensing apparatus or may be stored at another location, for instance, in an electronic medical record for the patient at a centralized data store. Because information is accessed for a number of patients, it's more likely that the information may be accessed from disparate sources. The patient profile information accessed at block 304 may include any of a variety of different medically-related information for each patient that may be used to determine medications for critical access override for each patient (i.e., any medications that may be needed for each patient in an emergency situation).

One or more medications are selected for critical access override for the group of patients based on the patient profile information for each of the patients, as shown at block 306. Generally, the system may analyze the patient profile information to predict what medications may be needed in an emergency situation for any of the patients from the group of patients.

The one or more medications are added to a critical access override list for the group of patients, as shown at block 308. In some instances, this may include generating a new critical access override list for the group of patients based on the identified one or more medications. In other instances, the one or more medications identified at block 306 are added to a standard critical access override list to create the critical access override list for the group of patients. The standard critical access override list may include a list of standard medications for which critical access override is provided as defined for a particular healthcare facility, a care unit, a particular medication dispensing apparatus, or other basis of standardization. In further embodiments, the one or more medications identified at block 306 are used to update an existing critical access override list for the group of patients. For instance, the critical access override list for the group of patients may be updated on a scheduled basis or based on some other triggering event (e.g., change in the patient profile information for a patient in the group of patients or based on the additional and/or removal of patients included in the group of patients). Updating a critical access override list may include adding and/or removing medications from the critical access override list. Any and all such combinations and variations are contemplated to be within the scope of embodiments of the present invention.

As noted above, the process of selecting medications for a critical access override list for a group of patients may be repeated as shown by the return to block 302 from block 308. For instance, the process may be performed on a periodic basis (e.g., hourly, daily, etc.) or when there is some other triggering event (e.g., change in the patient profile information for a patient in the group of patients or based on the additional and/or removal of patients included in the group of patients). When the process is repeated, new medications may be identified for the critical access override list and/or medications previously identified based on previous patient profile information may be removed based on the group of patients' current patient profile information.

As shown at block 310, after the critical access override list has been generated, a medication from the critical access override list may be selected for dispensing using a critical access override process.

Referring to FIG. 4, a flow diagram is provided that illustrates a method 400 for dynamically generating a critical access override list for a group of patients corresponding with a particular clinician in accordance with an embodiment of the present invention. As shown at block 402, a clinician is identified. In some embodiments, this may be done when a medication dispensing event is initiated by the clinician. For instance, a clinician may access a medication dispensing apparatus and enter clinician-identifying information to begin the process of dispensing medications from the medication dispensing apparatus. In other embodiments, the method 400 may be performed as a background process independent of any medication dispensing event by the clinician. In embodiments, the system may identify the clinician for performing the method 400 for dynamically determining medications for the clinician's personalized critical access override list on a periodic basis (e.g., hourly, daily, etc.) or when there is some other triggering event (e.g., a change to patients assigned to the clinician or a change to an electronic medical record or other patient information for a patient assigned to the clinician).

A group of patients being treated by the clinician is identified, as shown at block 404. The patients may be manually identified or automatically identified by the system as patients being treated by the clinician. Generally, any patient for which the clinician has some actions, duties, or other responsibilities may be identified as a patient being treated by the clinician.

The method 400 continues similarly to blocks 304, 306, 308 of the method 300 described above with reference to FIG. 3. In particular, patient profile information for each patient from the group of patients is accessed, as shown at block 406. One or more medications are identified for critical access override based on the patient profile information for the group of patients, as shown at block 408. The one or more medications are added to a critical access override list for the clinician, as shown at block 410. Additionally, the process may be repeated to update the clinician's critical access override list, as represented by the return to block 404 from block 410.

By generating a critical access override list for a clinician, medications on the critical access override list could be presented when a clinician accesses a medication dispensing apparatus. This may allow a clinician to quickly access a medication on the critical access override list via a critical access override dispensing. For instance, in an embodiment, the clinician may enter identifying information and/or a password (e.g., manually entering text, scanning a clinician barcode, or otherwise) and may be presented the medications on the critical access override list. The clinician may then simply select a medication for critical access override dispensing.

Turning now to FIG. 5, a flow diagram is provided that illustrates a method 500 for dynamically generating a critical access override list for a group of patients corresponding with a particular medication dispensing apparatus in accordance with an embodiment of the present invention. As shown at block 502, a medication dispensing apparatus is identified. In some embodiments, this may be done when a medication dispensing event is initiated at the medication dispensing apparatus. In other embodiments, the method 500 may be performed as a background process independent of any medication dispensing event at the medication dispensing apparatus. In embodiments, the system may identify the medication dispensing apparatus for performing the method 500 for dynamically determining medications for the critical access override list for the medication dispensing apparatus on a periodic basis (e.g., hourly, daily, etc.) or when there is some other triggering event (e.g., a change to patients corresponding with the medication dispensing apparatus or a change to an electronic medical record or other patient information for a patient corresponding with the medication dispensing apparatus).

A group of patients associated with the medication dispensing apparatus is identified, as shown at block 504. The patients may be manually identified or automatically identified by the system. Generally, a healthcare facility may define rules for determining which patients are associated with the medication dispensing apparatus. The rules may be based on, for instance, a likelihood that medications will be dispensed from the medication dispensing apparatus for the patients. For example, patients may be identified for a given medication dispensing apparatus based on the care unit to which the patients are assigned. As another example, the patients may be identified based on the physical proximity of the patients to the medication dispensing apparatus. In some instances, a patient's physical proximity to a medication dispensing apparatus could be based on a patient room to which the patient is assigned. In other instances, patients' locations may be tracked in real-time (e.g., by using RFIDs or other patient-location tracking approaches) and the patients' tracked location may be used to determine to associate the patient with a particular medication dispensing apparatus.

The method 500 continues similarly to blocks 304, 306, and 308 of the method 300 described above with reference to FIG. 3. In particular, patient profile information for each patient from the group of patients is accessed, as shown at block 506. One or more medications are identified for critical access override based on the patient profile information for the group of patients, as shown at block 508. The one or more medications are added to a critical access override list for the medication dispensing apparatus, as shown at block 510. Additionally, the process may be repeated to update the medication dispensing apparatus' critical access override list, as represented by the return to block 504 from block 510.

By generating a critical access override list for a medication dispensing apparatus, medications on the critical access override list could be presented when any clinician accesses the medication dispensing apparatus. This may allow a clinician to quickly access a medication on the critical access override list via a critical access override dispensing. For instance, in an embodiment, a clinician may enter identifying information and/or a password (e.g., manually entering text, scanning a clinician barcode, or otherwise) at a medication dispensing apparatus and may be presented the medications on the critical access override list for that medication dispensing apparatus. The clinician may then simply select a medication for critical access override dispensing.

It should be understood that combinations of the above approaches may be used for selecting groups of patients for a critical access override list. For example, a clinician may work in an area with multiple medication dispensing apparatuses and the process may determine critical access override lists for the clinician on a per medication dispensing apparatus basis (e.g., determine a group of patients associated with clinician and each particular medication dispensing apparatus). Additionally, other approaches for determining groups of patients for a critical access override list may be employed with the scope of embodiments of the present invention.

Additionally, although FIG. 4 was discussed with reference to a single clinician, in embodiments, a critical access override list may be generated for a group of clinicians (e.g., all clinicians in a particular area of a hospital) based on the groups of patient being treated by those clinicians. Likewise, although FIG. 5 was discussed with reference to a single medication dispensing apparatus, in embodiments, a critical access override list may be generated for a group of medication dispensing apparatuses based on the groups of patients associated with those medication dispensing apparatuses.

Figure 6:
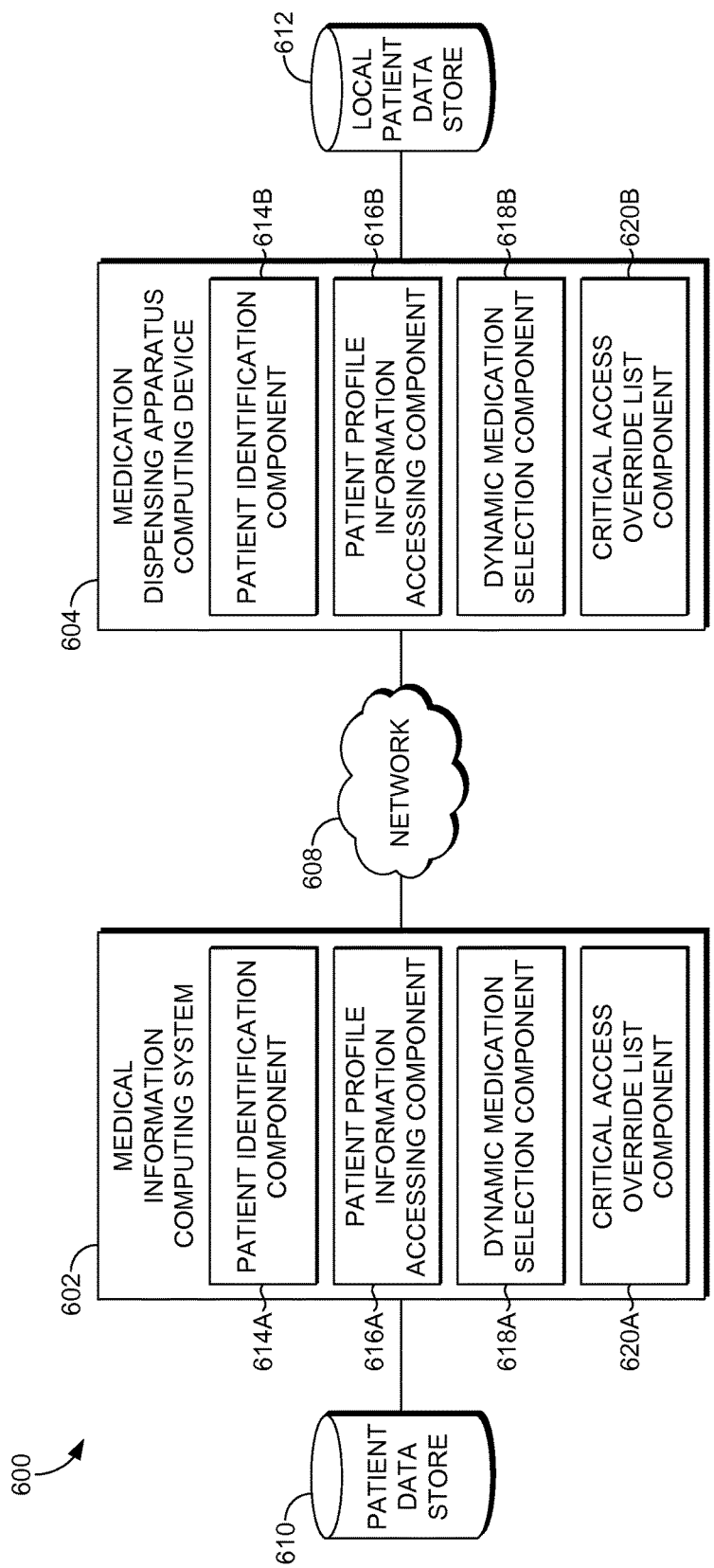
FIG. 6 is a block diagram of an exemplary system in which embodiments of the invention may be employed.

With reference now to FIG. 6, a block diagram is provided illustrating an exemplary system 600 in which embodiments of the present invention may be employed. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown, the system 600 may include a medical information computing system 602 and a medication dispensing apparatus computing device 604. The components may communicate with each other via a network 608, which may include, without limitation, one or more local area networks (LANs) and/or wide area networks (WANs). It should be understood that any number of medical information computing systems and medication dispensing apparatus computing devices may be employed within the system 600 within the scope of the present invention. Each may comprise a single device or multiple devices cooperating in a distributed environment. For instance, the medication information computing system 602 may comprise multiple devices arranged in a distributed environment that collectively provide the functionality of the medical information computing system 602 described herein. Additionally, other components not shown may also be included within the system 600.

The medical information computing system 602 may comprise a comprehensive medical information system, such as the system 200 described hereinabove with reference to FIG. 2. However, the medication information computing system 602 may take other forms in various embodiments of the invention. For instance, a single computing device could be provided for providing the functionality described herein.

As shown in FIG. 6, the medical information computing system 602 may include a patient identification component 614A, a patient profile information accessing component 616A, a dynamic medication selection component 618A, and a critical access override list component 620A. Generally, when a critical access override list is to be generated, the patient identification component 614A identifies a single patient or a group of patients for which the critical access override list is to be generated.

Based on the identified patient or group of patients, the patient profile information accessing component 616A accesses patient profile information for the single patient or each patient in the group of patients. The patient profile information accessing component 616A may access all patient profile information or only selected portions of patient profile information. Generally, the accessed information may include any demographic, medical, or other related information that may be useful in selecting medications for critical access override. In some embodiments, the patient profile accessing component 616A may access the patient profile information from a patient data store 610 that stores patient information for patients of a healthcare facility. For instance, the patient data store 610 may store electronic medical records for patients. In some embodiments, patient profile information may also be stored locally at medication dispensing apparatus computing devices, such as the local patient data store 612 associated with the medication dispensing apparatus computing device 604, and the patient profile information accessing component 616A may request information from such storage. In still other embodiments, the patient profile accessing component 616A may access patient profile information from other locations, such as cloud-based patient electronic medical records that may be available to multiple healthcare facilities. Any and all such combinations and variations are contemplated to be within the scope of embodiments of the present invention.

The dynamic medication selection component 618A analyzes patient profile information for a patient or group of patients to identify medications for which critical access override should be provided. The analysis may include identifying single pieces of patient information in isolation that may trigger selection of particular medications or multiple pieces of patient information together to identify particular medications. Various rules may be established to facilitate the selection of medications based on the patient profile information. The rules may be defined based on best practice information, medical literature, historical treatment information, and other resources that suggest certain medications may be needed in emergency situations given various patient conditions and other information.

The critical access override list component 620A generates a critical access override list based on the medications selected by the dynamic medication selection component 618A. In some instances, the critical access override list component 620A may generate a new critical access override list for the patient or group of patients, while in other instances, the critical access override list component 620A may update an existing critical access override list for the patient or group of patients. Updating an existing critical access override list may include adding and/or removing medications from the critical access override list. The critical access override list may be stored by the medical information computing system 602. Additionally, the medical information computing system 602 may communicate the critical access override list to one or more medication dispensing apparatus computing devices, such as the medication dispensing apparatus computing device 604, which are associated with medication dispensing apparatuses and control the dispensing of medications from the medication dispensing apparatuses. As such, critical access override may be provided for medications on the critical access override list.

As shown in FIG. 6, the medication dispensing apparatus computing device 604 may also include a patient identification component 614B, a patient profile information accessing component 616B, a dynamic medication selection component 618B, and a critical access override list component 620B. These components may operate in a similar manner to the components 614A, 616A, 618A, and 620A to allow for the generation of critical access override lists locally on the medication dispensing apparatus 604. Accordingly, in various embodiments of the present invention, critical access override lists may be generated locally at medication dispensing apparatuses (e.g., by medication dispensing apparatus computing device 604), by a backend system (e.g., by medical information computing system 602), or some other component. In some embodiments, various components may work in cooperation to generate a critical access override list. For instance, the medication dispensing apparatus 604 may perform some steps while the medication information computing system 602 may perform others to generate a particular critical access override list. Any and all such combinations and variations are contemplated to be within the scope of embodiments of the present invention.

As can be understood, embodiments of the present invention provide for dynamically generating critical access override lists based on patient profile information. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer-useable instructions that, when used by one or more computing devices, cause the one or more computing devices to perform operations, the operations comprising:
    accessing patient profile information for a patient;
    analyzing the patient profile information to predict one or more medications that may be needed in a future emergency situation for the patient involving a future patient condition not currently experienced by the patient;
    selecting, based on analyzing the patient profile information, one or more medications to allow for critical access override dispensing from a medication dispensing apparatus; and
    generating a personalized critical access override list for the patient that includes an identification of the one or more medications to allow for future critical access override dispensing of the one or more medications on the personalized critical access override list without requiring all steps required for a typical medication dispensing event from the medication dispensing apparatus.

2. The one or more computer storage media of claim 1, wherein the patient profile information is stored locally on the medication dispensing apparatus.

3. The one or more computer storage media of claim 1, wherein the patient profile information is stored in an electronic medical record for the patient in a central data store remote from the medication dispensing apparatus.

4. The one or more computer storage media of claim 1, wherein the operations further comprise:
    accessing the personalized critical access override list for the patient in response to a clinician initiating a medication dispensing event subsequent to generating the personalized critical access override list that includes the identification of the one or more medications; and
    dispensing a medication identified on the personalized critical access override list using a critical access override.

5. The one or more computer storage media of claim 1, wherein the one or more medications are selected and the personalized critical access override list for the patient is generated in a background process independent of any medication dispensing event and the personalized critical access override list is stored.

6. The one or more computer storage media of claim 1, wherein the one or more medications are selected and the personalized critical access override list for the patient is generated during a medication dispensing event for the identified patient.

7. The one or more computer storage media of claim 1, wherein generating the personalized critical access override list for the patient comprises adding the one or more medications to a standard critical access override list with one or more other medications to create the personalized critical access override list for the patient.

8. The one or more computer storage media of claim 7, wherein the one or more other medications in the standard critical access override list are standard for one selected from the following: a healthcare facility, a care unit, and a medication dispensing apparatus.

9. The one or more computer storage media of claim 1, wherein generating the personalized critical access override list for the patient comprises generating a new personalized critical access override list for the patient.

10. The one or more computer storage media of claim 1, wherein the patient profile information includes one or more selected from the following: a diagnosis, a currently prescribed medication, an allergy, age of the patient, gender of the patient, and/or ethnicity of the patient.

11. A computer-implemented method for dynamically determining medications for a critical access override list for a group of patients, the method comprising:
    accessing, from an electronic data store, patient profile information for each patient from the group of patients;
    analyzing the patient profile information to predict one or more medications that may be needed in a future emergency situation involving a future condition for any patient from the group of patients;
    selecting, based on analyzing the patient profile information, the one or more medications for critical access override dispensing from a medication dispensing apparatus; and
    generating a critical access override list for the group of patients that includes an identification of the one or more medications to allow for future critical access override dispensing of the one or more medications without requiring all steps required for a typical medication dispensing event from the medication dispensing apparatus.

12. The method of claim 11, wherein the patient profile information is stored locally on the medication dispensing apparatus.

13. The method of claim 11, wherein identifying the group of patients comprises:
   identifying a clinician; and
   identifying patients being treated by the identified clinician as the group of patients.

14. The method of claim 13, wherein the critical access override list is specific to the clinician and provided when the clinician accesses a medication dispensing apparatus.

15. The method of claim 14, wherein the critical access override list is generated in response to the clinician accessing a medication dispensing apparatus.

16. The method of claim 14, wherein the critical access override list is generated in a background process independent of any medication dispensing event and the critical access override list is stored.

17. The method of claim 11, wherein the method further comprises providing the critical access override list when any clinician accesses the medication dispensing apparatus.

18. The method of claim 11, wherein the method further comprises:
   accessing the critical access override list for the group of patients in response to a clinician initiating a medication dispensing event subsequent to generating the critical access override list that includes the identification of the one or more medications; and
   dispensing a medication identified on the personalized critical access override list using a critical access override.

19. A system for providing dynamic critical access override lists for medication dispensing, the system including one or more processors and comprising:
   one or more processors; and
   one or more computer storage media storing computer-useable instructions that, when used by the one or more processors, cause the one or more processors to:
   access patient profile information for a single patient or a group of patients;
   analyze the patient profile information to predict one or more medications that may be needed in a future emergency situation involving a patient condition not currently experienced by the single patient or any patient from the group of patients and select the one or more medications for critical access override based on analyzing the patient profile information; and
   generate a critical access override list that includes an identification of the one or more medications to allow for future critical access override dispensing of the one or more medications on the personalized critical access override list without requiring all steps required for a typical medication dispensing event from the medication dispensing apparatus.

20. The system of claim 19, wherein the system is located on a medication dispensing apparatus computing device operable to control dispensing of medications from a corresponding medication dispensing apparatus.

* * * * *